United States Patent
Bon et al.

(10) Patent No.: US 8,884,033 B2
(45) Date of Patent: Nov. 11, 2014

(54) PROCESS FOR PREPARING AMINOBENZOYLBENZOFURAN DERIVATIVES

(71) Applicant: Sanofi, Paris (FR)

(72) Inventors: Xavier Bon, Paris (FR); Christine Biencourt, Paris (FR); Corinne Leroy, Paris (FR); Julia Mateos-Caro, Paris (FR); Philippe Vayron, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/742,816

(22) Filed: Jan. 16, 2013

(65) Prior Publication Data

US 2013/0165675 A1  Jun. 27, 2013

Related U.S. Application Data

(63) Continuation of application No. PCT/FR2011/051710, filed on Jul. 18, 2011.

(30) Foreign Application Priority Data

Jul. 19, 2010 (FR) ..................... 10 55824

(51) Int. Cl.
| C07D 307/00 | (2006.01) |
| A61K 31/343 | (2006.01) |
| C07D 307/80 | (2006.01) |

(52) U.S. Cl.
CPC ............ *A61K 31/343* (2013.01); *C07D 307/80* (2013.01)
USPC ....................................................... 549/468

(58) Field of Classification Search
USPC ....................................................... 549/468
See application file for complete search history.

(56) References Cited

U.S. PATENT DOCUMENTS

| 5,223,510 | A  | 6/1993  | Gubin et al. |
| 6,828,448 | B2 | 12/2004 | Fino et al. |
| 6,846,936 | B2 | 1/2005  | Biard |
| 2012/0065411 | A1 | 3/2012 | Kretzschmar et al. |
| 2012/0077995 | A1 | 3/2012 | Kretzschmar et al. |
| 2012/0289717 | A1 | 11/2012 | Friesz et al. |
| 2012/0330036 | A1 | 12/2012 | Friesz et al. |
| 2013/0012729 | A1 | 1/2013  | Bailly et al. |

FOREIGN PATENT DOCUMENTS

| EP | 0471609 | 2/1992 |
| WO | WO 02/48078 | 6/2002 |
| WO | WO 02/48132 | 6/2002 |
| WO | WO 2012/010802 | 1/2012 |
| WO | WO 2012/127173 | 9/2012 |
| WO | WO 2012/131408 | 10/2012 |
| WO | WO 2012/131409 | 10/2012 |
| WO | WO 2012/131410 | 10/2012 |

OTHER PUBLICATIONS

Bavin, Org. Syn. Coll. vol. 5 pp. 30 (1973).*
Wikipedia, the free encyclopedia Nov. 5, 2012.*
Schotten et al Syn. (2002) pp. 1607-1610.*
U.S. Appl. No. 13/638,484, filed Aug. 30, 2012, Bailly, et al.
U.S. Appl. No. 13/638,500, filed Sep. 28, 2012, Priem, et al.
U.S. Appl. No. 13/628,867, filed Sep. 27, 2012, Bon, et al.
U.S. Appl. No. 13/711,891, filed Dec. 12, 2012, Friesz.
U.S. Appl. No. 13/740,505, filed Jan. 14, 2013, Friesz, et al.
International Search Report for WO2012/010788 dated Jan. 26, 2012.

* cited by examiner

*Primary Examiner* — Andrew D Kosar
*Assistant Examiner* — Raymond Covington
(74) *Attorney, Agent, or Firm* — Scully, Scott, Murphy & Presser, P.C.

(57) ABSTRACT

The disclosure relates to a process for preparing 5-aminobenzoylbenzofuran derivatives of formula I:

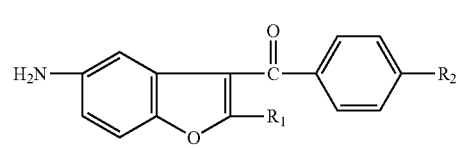

in which $R_1$ and $R_2$ are as defined in the disclosure; by reduction of a 5-nitrobenzofuran derivative of formula II:

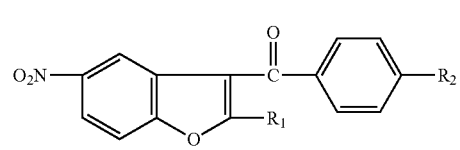

using a hydrogen transfer agent, in the presence of palladium-on-charcoal as catalyst and in an ether or an ether mixture as solvent.

16 Claims, No Drawings

PROCESS FOR PREPARING AMINOBENZOYLBENZOFURAN DERIVATIVES

This application is a continuation of International Application No. PCT/FR2011/051710, filed Jul. 18, 2011, which is incorporated herein by reference in its entirety; which claims the benefit of priority of French Patent Application No. 1055824, filed Jul. 19, 2010.

The present invention relates generally to the preparation of amino-benzoyl-benzofuran derivatives.

More specifically, the invention relates to a process for the preparation of 5-amino-benzoyl-benzofuran derivatives of general formula:

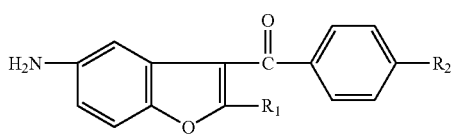

I in which $R_1$ represents hydrogen or an alkyl group and $R_2$ represents hydrogen or an alkyl, alkoxy or dialkylaminoalkoxy group.

In the above formula I:
$R_1$ represents in particular a linear or branched $C_1$-$C_8$ alkyl group, in particular a linear or branched $C_1$-$C_4$ alkyl group, such as methyl, ethyl, n-propyl, isopropyl, n-butyl, sec-butyl or tert-butyl,
$R_2$ represents in particular a linear or branched $C_1$-$C_8$ alkyl group, in particular a linear or branched $C_1$-$C_4$ alkyl group, such as methyl, ethyl, n-propyl, isopropyl, n-butyl, sec-butyl or tert-butyl; a linear or branched $C_1$-$C_8$ alkoxy group, in particular a linear or branched $C_1$-$C_4$ alkoxy group, such as methoxy, ethoxy, n-propoxy, isoproxy, n-butoxy, sec-butoxy or tert-butoxy; or also a dialkylaminoalkoxy group in which each linear or branched alkyl group is a $C_1$-$C_8$ alkyl group and the linear or branched alkoxy group is a $C_1$-$C_8$ alkoxy group, in particular in which each linear or branched alkyl group is a $C_1$-$C_4$ alkyl group, such as methyl, ethyl, n-propyl, isopropyl, n-butyl, sec-butyl or tert-butyl, and the linear or branched alkoxy group is a $C_1$-$C_4$ alkoxy group, such as methoxy, ethoxy, n-propoxy, isopropoxy, n-butoxy, sec-butoxy or tert-butoxy.

Preferably, $R_1$ represents n-butyl and $R_2$ represents 3-[di(n-butyl)amino]propoxy.

The compounds of formula I above are, for the most part, compounds described in patent EP 0 471 609, where they are presented as intermediates in the final preparation of aminoalkoxybenzoyl-benzofuran derivatives of use for their therapeutic applications in the cardiovascular field.

Among these aminoalkoxybenzoyl-benzofuran derivatives, 2-(n-butyl)-3-(4-{3-[di(n-butyl)amino]propoxy}benzoyl)-5-(methanesulfonamido benzofuran, commonly referred to as dronedarone, and its pharmaceutically acceptable salts, has proven to be particularly advantageous, in particular as antiarrhythmic agent.

A process for the preparation of dronedarone was reported in the above said patent EP 0 471 609, according to which process 2-(n-butyl)-3-(4-{3-[di(n-butyl)amino]propoxy}benzoyl)-5-nitrobenzofuran is reduced under pressure with hydrogen in the presence of platinum oxide as catalyst to form 2-(n-butyl)-3-(4-{3-[di(n-butyl)amino]propoxy}benzoyl)-5-aminobenzofuran (hereinafter Compound A), which is subsequently treated with methanesulfonyl chloride, in the presence of an acid acceptor, to give the desired compound. According to this process, dronedarone could be obtained with an overall yield of the order of 60%, starting from the 5-nitrobenzofuran derivative.

However, this process is not devoid of disadvantages inherent in particular in the type of reaction used in the formation of Compound A, namely a hydrogenation under pressure, which has an industrial risk.

Moreover, this method requires the isolation of Compound A from its formation medium, the isolation of this compound, normally in the form of its oxalate, consequently constituting an additional stage in the preparation of dronedarone.

The search for an industrial preparation process capable of overcoming these disadvantages while offering high yields of Compound A and also facilitated use of the latter, so as to produce significantly greater yields of dronedarone with respect to the prior process, consequently remains of indisputable interest.

In point of fact, it has now been found that Compound A can be prepared according to a process involving a selective reduction of its nitro functional group with respect to its ketone functional group. This selective reduction consequently eliminates the need to isolate this Compound A via its oxalate during the final synthesis of dronedarone, which can be obtained in this way with overall yields of greater than 90% from the starting 5-nitrobenzofuran derivative.

The aminoalkoxybenzoyl-benzofuran derivatives of patent EP 0 471 609, in particular dronedarone, can consequently be synthesized in the very medium for formation of the appropriate compound of formula I.

According to a first subject matter of the invention, the 5-aminobenzofuran derivatives of formula I can be prepared by reducing a 5-nitrobenzofuran derivative of general formula:

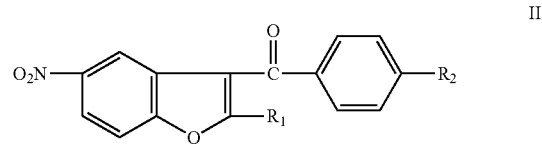

II in which $R_1$ and $R_2$ have the same meanings as above, by means of a hydrogen-transfer agent, in the presence of palladium-on-charcoal as catalyst and in an ether or a mixture of ethers as solvent, which forms the desired compounds.

In the above formula II, $R_1$ preferably represents n-butyl and $R_2$ preferably represents 3-[di(n-butyl)amino]propoxy.

In addition, according to another of its subject matters, the invention relates to a process for the preparation of sulfonamidobenzofuran derivatives of general formula:

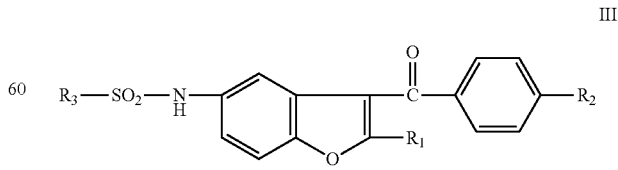

III and of their pharmaceutically acceptable salts, in which $R_1$ and $R_2$ have the same meanings as above and $R_3$ represents an alkyl group, according to which process:

a) a 5-nitrobenzofuran derivative of formula II is reduced by means of a hydrogen-transfer agent, in the presence of palladium-on-charcoal as catalyst and in an ether or a mixture of ethers as solvent, in order to form a reaction medium comprising a 5-amino-benzoyl-benzofuran derivative of formula I above, in the free base form, b) the reaction medium comprising the 5-amino-benzoyl-benzofuran derivative of formula I in the free base form obtained above is treated with a halide of general formula:

    IV in which Hal represents a halogen, such as chlorine, and $R_3$ has the same meaning as above, in the presence of a basic agent, in order to obtain the desired compounds in the free base form, which are reacted, if necessary, with an organic or inorganic acid in order to form a pharmaceutically acceptable salt of this desired compound.

Subsequently, the pharmaceutically acceptable salt of the compound of formula III can be recovered from its formation medium, for example by crystallization.

In the above formula III, $R_3$ represents in particular a linear or branched $C_1$-$C_8$ alkyl group, in particular a linear or branched $C_1$-$C_4$ alkyl group, such as methyl, ethyl, n-propyl, isopropyl, n-butyl or tert-butyl, Preferably, $R_1$ represents n-butyl, $R_2$ represents 3-[di(n-butyl)amino]propoxy and $R_3$ represents methyl in the above formula III.

The hydrogen transfer reduction according to the invention is normally carried out in an ether or a mixture of ethers as solvent, in contrast to the state of the art, where this type of reaction is generally carried out in an alcohol. This reduction in an ether or a mixture of ethers makes possible in particular a significant chemoselectivity of the nitro functional group at the expense of the ketone functional group which is also present and which is itself also capable of a reduction to give alcohol. This selective reduction of the nitro functional group consequently avoids the isolation of the compound of formula I in whatever way this is done, in particular by conversion of this compound, obtained in basic form, into a salt which can be easily separated from its formation medium.

The ether used as solvent is usually a dialkyl ether, such as methyl tert-butyl ether, or a cyclic ether, for example tetrahydrofuran, while the mixture of ethers generally corresponds to a mixture of dialkyl ether and of cyclic ether, for example a mixture of methyl tert-butyl ether and of tetrahydrofuran.

Methyl tert-butyl ether represents a solvent which is particularly preferred in the context of the present invention, in particular for the preparation of Compound A and subsequently of dronedarone.

Usually, the hydrogen-transfer agent is a formate, preferably ammonium formate, or a phosphinate, in particular sodium phosphinate. This hydrogen-transfer agent is used in excess with respect to the compound of formula II, it being possible for this excess to reach from 3 to 5 equivalents, or more, of hydrogen-transfer agent per equivalent of compound of formula II. Preferably, 5 or approximately 5 equivalents of hydrogen-transfer agent are used per equivalent of compound of formula II, for example 5 or approximately 5 equivalents of hydrogen-transfer agent dissolved, for example, in a volume of water. In particular, 5 equivalents of ammonium formate dissolved, for example, in a volume of water are used.

The reduction can take place at ambient temperature. However, the reduction is generally undertaken by heating the reaction medium at a temperature ranging up to, for example, from 50° C. to 60° C., preferably at a temperature of the order of 40° C., in particular at 40° C.

According to one of its specific aspects, the invention additionally relates to a process for the preparation of 2-(n-butyl)-3-(4-{3-[di(n-butyl)amino]propoxy}benzoyl)-5-aminobenzofuran, according to which process 2-(n-butyl)-3-(4-{3-[di(n-butyl)amino]propoxy}benzoyl)-5-nitrobenzofuran is reduced by means of ammonium formate or sodium phosphinate as hydrogen-transfer agent, in the presence of palladium-on-charcoal as catalyst and in methyl tert-butyl ether or a mixture of methyl tert-butyl ether and of tetrahydrofuran as solvent, to form a reaction medium comprising 2-(n-butyl)-3-(4-{3-[di(n-butyl)amino]propoxy}benzoyl)-5-aminobenzofuran in the free base form.

Moreover, according to another of its specific aspects, the invention relates to a process for the preparation of 2-(n-butyl)-3-(4-{3-[di(n-butyl)amino]propoxy}benzoyl)-5-(methanesulfonamido)benzofuran or dronedarone and of its pharmaceutically acceptable salts, according to which process:

a) 2-(n-butyl)-3-(4-{3-[di(n-butyl)amino]propoxy}benzoyl)-5-nitrobenzofuran is reduced by means of ammonium formate or sodium phosphinate as hydrogen-transfer agent, in the presence of palladium-on-charcoal as catalyst and in methyl tert-butyl ether or a mixture of methyl tert-butyl ether and of tetrahydrofuran as solvent, in order to form a reaction medium comprising 2-(n-butyl)-3-(4-{3-[di(n-butyl)amino]propoxy}benzoyl)-5-aminobenzofuran in the free base form, b) the reaction medium comprising the 2-(n-butyl)-3-(4-{3-[di(n-butyl)amino]propoxy}benzoyl)-5-aminobenzofuran in the free base form obtained above is treated with a methanesulfonyl halide in the presence of a basic agent, in order to obtain the dronedarone in the basic form, which is reacted, if necessary, with an organic or inorganic acid in order to form a pharmaceutically acceptable salt of dronedarone.

Subsequently, the pharmaceutically acceptable salt of dronedarone can be recovered from its formation medium, for example by crystallization.

In the light of the preceding description, the combination formed by a 5-nitrobenzofuran derivative of formula II, a hydrogen-transfer agent, palladium-on-charcoal and an ether or a mixture of ethers as solvent proves to be particularly advantageous as reaction medium for the preparation of various compounds, in particular the compounds of formula I and those of formula III above.

Consequently, another subject matter of the invention relates to a reaction medium, characterized in that it is formed:

a) of a 5-nitrobenzofuran derivative of formula II, in particular a derivative of formula II in which $R_1$ represents n-butyl and $R_2$ represents 3-[di(n-butyl)amino]propoxy, b) of a hydrogen-transfer agent, such as ammonium formate or sodium phosphinate, c) of palladium-on-charcoal, d) of an ether, such as methyl tert-butyl ether, or of a mixture of ethers, such as a mixture of methyl tert-butyl ether and of tetrahydrofuran, as solvent.

The following non-limiting example illustrates the preparation of a compound of formula I according to the process of the invention and also its use in the synthesis of dronedarone.

EXAMPLE a) 2-(n-Butyl)-3-(4-{3-[di(n-butyl)amino]propoxy}benzoyl)-5-aminobenzofuran (Compound A or compound of formula I: $R_1$=n-$C_4H_9$; $R_2$=3-[di(n-butyl)amino]propoxy)

3.33 kg of a 30% solution of 2-(n-butyl)-3-(4-{3-[di(n-butyl)amino]propoxy}benzoyl)-5-nitrobenzofuran (compound of formula II) and 0.05 kg of dry palladium-on-charcoal (Pd/C) are charged to a 5 l reactor at ambient temperature. The combined mixture is heated, with stirring, to 40° C. and then a solution of 0.62 kg (5 equivalents) of ammonium formate in 0.62 kg of water is added over approximately 2 h. The temperature of the reaction medium is then maintained at 40° C. (+/−2° C.) for 15 h while monitoring the progress of the reaction by liquid chromatography. As soon as the reduction is complete, the mixture is cooled to 23° C. (+/−2° C.) and then the palladium-on-charcoal is filtered off and then washed with methyl tert-butyl ether and water. Separation by settling is then carried out at ambient temperature and the organic phase is washed with water. These operations of separation by settling and washing are subsequently repeated once. A further separation by settling is carried out and the solution is concentrated at 40° C. under vacuum. The concentrate is subsequently diluted with tetrahydrofuran, which provides 3.47 kg of a solution of the desired compound in a mixture of methyl tert-butyl ether and of tetrahydrofuran. Estimated yield: 99% b) Dronedarone hydrochloride (hydrochloride of the compound of formula III: $R_1$=n-$C_4H_9$; $R_2$=3-[di(n-butyl)amino]propoxy; $R_3$=$CH_3$)

The 3.47 kg of solution of Compound A in a mixture of methyl tert-butyl ether and of tetrahydrofuran obtained above is charged to a 5 l reactor at ambient temperature. The methanesulfonyl chloride is subsequently added over 1 h with stirring while maintaining the temperature of the reaction medium below 30° C. Cooling is carried out to 25° C. and then an aqueous ammonia solution is run in, the temperature of the reaction medium being maintained at 25° C. The end of the reaction is monitored by liquid chromatography. Water and methyl tert-butyl ether are then added to the reaction medium, maintained at 30° C., and stirring is maintained for 15 min. After separation by settling, the organic phase is washed, first with an aqueous saline solution. Stirring is maintained at 28° C. for 10 min, separation by settling is then carried out and the organic phase is concentrated at 45° C. under vacuum. Isopropanol is then added and the solution is concentrated at 50° C. under vacuum. Isopropanol is again added and the solution is again concentrated at 50° C. under vacuum. The reaction medium is adjusted by addition of 2.03 kg of isopropanol, so as to obtain 3.62 kg of a solution, in isopropanol, of the desired compound in the base form. This solution is heated to 50° C., 0.225 kg of hydrochloric acid is then added to the reaction medium, maintained at a temperature of 50° C. to 55° C., and then the crystallization of the desired hydrochloride is initiated by addition of dronedarone hydrochloride to the reaction medium. The product is subsequently filtered off and the filtration cake is washed with isopropanol, which provides the desired hydrochloride, which is dried at 45° C. under vacuum in order to obtain 1.12 kg of dry dronedarone hydrochloride.

Overall yield (with respect to the compound I): 96%

The process according to the invention exhibits indisputable advantages in comparison with the method described in patent EP 0 471 609 or patent application WO 2002/048078.

This is because the nitro functional group of the compound of formula II can be reduced in a standard reactor, which avoids the need to operate with hydrogen under pressure in a hydrogenation device. Moreover, the quality of the compound of formula I in the base form is found to be significantly improved since a reduced number of various impurities are recorded as being formed, and in smaller contents. This advantage makes it possible to avoid the preparation and the isolation of the oxalate of the compound of formula I, which operation presents numerous problems on the industrial scale.

In addition, the use of the non-isolated compounds of formula I in a process for the preparation of the pharmacologically active aminoalkoxybenzoyl-benzofuran derivatives of the patent EP 0 471 609 and in particular in a process for the preparation of the compounds of formula III above makes it possible to very significantly improve the yield of this process. In the specific case of dronedarone, the overall yield of its synthesis, starting from its corresponding 5-nitrobenzofuran derivative, rises from 60%, according to the state of the art, to 95% by the use of the chemoselective process of the invention. This improvement is related in particular to the absence of isolation of the oxalate of the compound of formula I and to the losses associated therewith.

What is claimed is:

1. A process for the preparation of a 5-amino-benzoyl-benzofuran derivative of formula I:

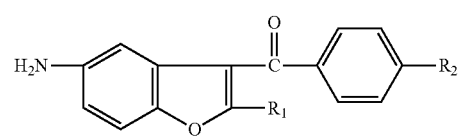

in which $R_1$ represents hydrogen or an alkyl group and $R_2$ represents hydrogen or an alkyl, alkoxy or dialkylaminoalkoxy group, comprising reducing a 5-nitrobenzofuran derivative of formula II:

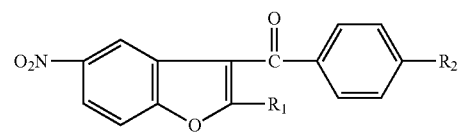

in which $R_1$ and $R_2$ have the same meanings as above, by means of a hydrogen-transfer agent, in the presence of palladium-on-charcoal as catalyst and in an ether or a mixture of ethers as solvent, which forms the desired compound.

2. A process for the preparation of a sulfonamidobenzofuran derivative of formula III:

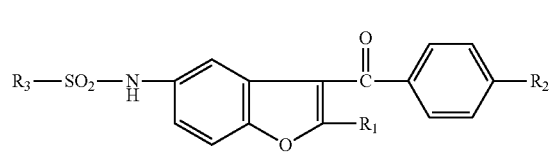

or a pharmaceutically acceptable salt thereof, in which $R_1$ represents hydrogen or an alkyl group, $R_2$ represents hydrogen or an alkyl, alkoxy or dialkylaminoalkoxy group and $R_3$ represents an alkyl group, comprising:

a) reducing a 5-nitrobenzofuran derivative of formula II:

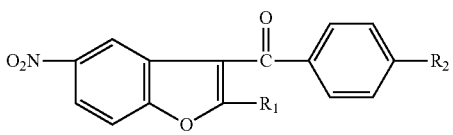

in which $R_1$ and $R_2$ have the same meanings as above,
by means of a hydrogen-transfer agent, in the presence of palladium-on-charcoal as catalyst and in an ether or a mixture of ethers as solvent, in order to form a reaction medium comprising a 5-amino-benzoyl-benzofuran derivative, in the free base form, of formula I:

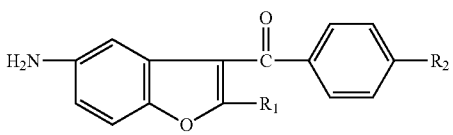

in which $R_1$ and $R_2$ have the same meanings as above; and b) treating the reaction medium comprising the 5-aminobenzoyl-benzofuran derivative of formula I in the free base form obtained above with a halide of formula IV:

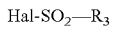

in which Hal represents a halogen and $R_3$ has the same meaning as above, in the presence of a basic agent; and reacting the obtained compound in the free base form, if necessary, with an organic or inorganic acid in order to form a pharmaceutically acceptable salt of the desired compound.

3. The process according to claim 1 or 2, wherein:
$R_1$ represents a linear or branched $C_1$-$C_8$ alkyl group;
$R_2$ represents a linear or branched $C_1$-$C_8$ alkyl group, a linear or branched $C_1$-$C_8$ alkoxy group or a dialkylaminoalkoxy group in which each linear or branched alkyl group is a $C_1$-$C_8$ alkyl group and the linear or branched alkoxy group is a $C_1$-$C_8$ alkoxy group; and
$R_3$ represents a linear or branched $C_1$-$C_8$ alkyl group.

4. The process as claimed in claim 1 or 2, wherein:
$R_1$ represents a linear or branched $C_1$-$C_4$ alkyl group;
$R_2$ represents a linear or branched $C_1$-$C_4$ alkyl group, a linear or branched $C_1$-$C_4$ alkoxy group or a dialkylaminoalkoxy group in which each linear or branched alkyl group is a $C_1$-$C_4$ group and the linear or branched alkoxy group is a $C_1$-$C_4$ group; and
$R_3$ represents a linear or branched $C_1$-$C_4$ alkyl group.

5. The process as claimed in claim 1 or 2, wherein $R_1$ represents n-butyl; $R_2$ represents 3-[di(n-butyl)amino]propoxy; and $R_3$ represents methyl.

6. The process as claimed in claim 1 or 2, wherein the hydrogen-transfer agent is a formate or a phosphinate.

7. The process as claimed in claim 6, wherein the formate is ammonium formate and the phosphinate is sodium phosphinate.

8. The process as claimed in claim 1 or 2, wherein the hydrogen-transfer agent is used in excess with respect to the compound of formula II.

9. The process as claimed in claim 8, wherein the hydrogen-transfer agent is used in a proportion of 5 equivalents per equivalent of compound of formula II.

10. The process as claimed in claim 1 or 2, wherein the ether is a dialkyl ether, a cyclic ether or a mixture of these.

11. The process as claimed in claim 10, wherein the dialkyl ether is methyl tert-butyl ether and the cyclic ether is tetrahydrofuran.

12. The process as claimed in claim 1 or 2, wherein the reduction takes place at a temperature ranging from ambient temperature to 50° C. to 60° C.

13. The process as claimed in claim 1 for the preparation of 2-(n-butyl)-3-(4-{3-[di(n-butyl)amino]propoxy}benzoyl)-5-aminobenzofuran, comprising reducing 2-(n-butyl)-3-(4-{3-[di(n-butyl)amino]propoxy}benzoyl)-5-nitrobenzofuran by means of ammonium formate or sodium phosphinate as hydrogen-transfer agent, in the presence of palladium-on-charcoal as catalyst and in methyl tert-butyl ether or a mixture of methyl tert-butyl ether and of tetrahydrofuran as solvent, to form 2-(n-butyl)-3-(4-{3-[di(n-butyl)amino]propoxy}benzoyl)-5-aminobenzofuran in the free base form.

14. The process as claimed in claim 2 for the preparation of 2-(n-butyl)-3-(4-{3-[di(n-butyl)amino]propoxy}benzoyl)-5-(methanesulfonamido)benzofuran or dronedarone or a pharmaceutically acceptable salt thereof, comprising:
a) reducing 2-(n-butyl)-3-(4-{3-[di(n-butyl)amino]propoxy}benzoyl)-5-nitrobenzofuran by means of ammonium formate or sodium phosphinate as hydrogen-transfer agent, in the presence of palladium-on-charcoal as catalyst and in methyl tert-butyl ether or a mixture of methyl tert-butyl ether and of tetrahydrofuran as solvent, in order to form 2-(n-butyl)-3-(4-{3-[di(n-butyl)amino]propoxy}benzoyl)-5-aminobenzofuran in the free base form,
b) treating the reaction medium comprising the 2-(n-butyl)-3-(4-{3-[di(n-butyl)amino]propoxy}benzoyl)-5-aminobenzofuran in the free base form obtained above with a methanesulfonyl halide in the presence of a basic agent, in order to obtain the dronedarone in the basic form, and reacting said dronedarone, if necessary, with an organic or inorganic acid in order to form a pharmaceutically acceptable salt of dronedarone.

15. A reaction medium comprising:
a) a 5-nitrobenzofuran derivative of formula II:

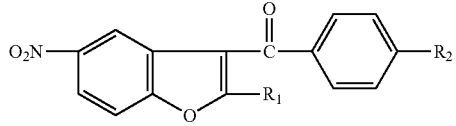

in which $R_1$ represents hydrogen or an alkyl group, and $R_2$ represents hydrogen or an alkyl, alkoxy or dialkylaminoalkoxy group;
b) a hydrogen-transfer agent;
c) palladium-on-charcoal; and
d) an ether or of a mixture of ethers, as solvent.

16. The reaction medium as claimed in claim 15, wherein $R_1$ represents n-butyl and $R_2$ represents 3-[di(n-butyl)amino]propoxy.

* * * * *